United States Patent [19]

Ishikawa

[11] Patent Number: 4,946,613
[45] Date of Patent: Aug. 7, 1990

[54] PHOTOSETTING FERROFLUID COMPOSITIONS

[75] Inventor: Yuichi Ishikawa, Yokohama, Japan

[73] Assignee: Nippon Seiko Kabushiki Kaisha, Tokyo, Japan

[21] Appl. No.: 173,724

[22] Filed: Mar. 25, 1988

[30] Foreign Application Priority Data

Mar. 27, 1987 [JP] Japan ................... 62-73655

[51] Int. Cl.$^5$ ............................ G01N 27/84
[52] U.S. Cl. ................. 252/62.52; 252/62.54
[58] Field of Search ........ 252/62.54, 62.51 R, 252/62.52

[56] References Cited

U.S. PATENT DOCUMENTS

| | | | |
|---|---|---|---|
| 3,862,047 | 1/1975 | Weltman et al. | 252/62.54 |
| 4,356,098 | 10/1982 | Chagnon | 252/62.51 R |
| 4,448,846 | 5/1984 | Chang et al. | 252/62.54 |
| 4,526,836 | 7/1985 | Mukai et al. | 252/62.54 |
| 4,526,837 | 7/1985 | Ohtsuki et al. | 252/62.54 |
| 4,560,616 | 12/1985 | Okita et al. | 252/62.54 |
| 4,560,617 | 12/1985 | Nishimatsu et al. | 252/62.54 |
| 4,601,947 | 7/1986 | Shimada et al. | 252/62.54 |
| 4,614,687 | 9/1986 | Nishimatsu et al. | 252/62.54 |
| 4,619,855 | 10/1986 | Okita et al. | 252/62.54 |
| 4,634,633 | 1/1987 | Ninomiya et al. | 252/62.54 |
| 4,678,708 | 7/1987 | Shimada et al. | 252/62.54 |
| 4,690,870 | 9/1987 | Okita et al. | 252/62.54 |
| 4,698,280 | 10/1987 | Mine et al. | 252/62.54 |
| 4,708,909 | 11/1987 | Ohtsuki et al. | 252/62.54 |
| 4,713,293 | 12/1987 | Asano et al. | 252/62.54 |
| 4,732,813 | 3/1988 | Huisman et al. | 252/62.54 |
| 4,734,326 | 3/1988 | Nishimatsu et al. | 428/694 |

FOREIGN PATENT DOCUMENTS

| | | | |
|---|---|---|---|
| 141547 | 9/1982 | Japan | 252/62.52 |
| 2620 | 8/1983 | PCT Int'l Appl. | 252/62.54 |

*Primary Examiner*—Jeffrey E. Russel
*Attorney, Agent, or Firm*—Basile and Hanlon

[57] ABSTRACT

Photosetting ferrofluid compositions of this type comprises three manners of structural feature.

A first type of the compositions to solve the problems mentioned above is a photosetting type ferrofluid which is prepared by admixing photosetting resin with ferrofluid in which ferromagnetic particles having adsorbed a surfactant(s) are dispersed into a carrier.

An improved photosetting type ferrofluid is also proposed as a second type of composition, in which the carrier itself is composed of at least a photosetting resin.

A further improved photosetting type ferrofluid having higher sensitivity than that of the second embodiment is also prepared as a type of composition, with an intention to obtain higher sharp microphotograph image, and this sensitive photosetting type ferrofluid is prepared by admixing a ferrofluid, consisting of a carrier of low viscosity, ferromagnetic particles, a surfactant or surfactants for dispersing the ferromagnetic particles in said carrier and further added with photosetting resin at least 25% by volume of the carrier.

5 Claims, 1 Drawing Sheet

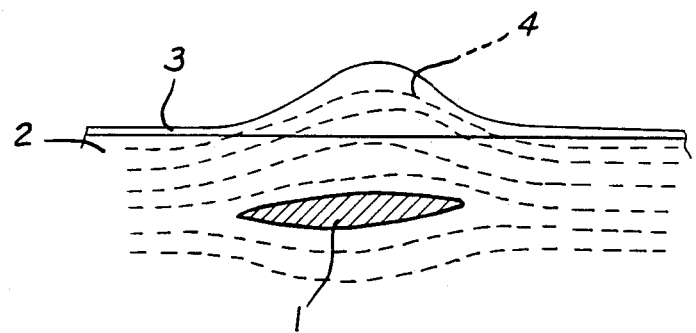

PHOTOSETTING FERROFLUID COMPOSITIONS

BACKGROUND OF THE INVENTION

1. Field of the Invention

This invention relates to photosetting magnetic colloids to be suitably used to visualize the recorded pattern of magnetic discs, photomagnetic discs or to magnetic flaw detection.

2. Description of the Prior Art

Ferrofluid compositions have widely been used as a conventional medium for magnetic flaw detection. Such ferrofluids are used by applying them onto the surface of the article or parts to be inspected so as to detect whether and where exists any flaw or defect in the article or parts.

It is very difficult for a mere micrographic examination to find out such defect when fine cracks, scratches or foreign matter are located very close to the surface of the article.

Once a magnetic field is formed in the article to be inspected the magnetic field will become nonuniform at the location of a defect because the magnetic flux leaks at the location of such defect. If ferrofluid is applied to the surface of article to be inspected, the applied ferrofluid will be attracted to the portion where magnetic flux leaks and will swell to form a pattern corresponding to the configuration of the defect portion.

It is widely recognized that the finer the ferromagnetic particles, the greater the sensitivity of the ferrofluid and thus the accuracy of magnetic flat detection can also be improved.

Indeed, when the particle diameter of the ferromagnetic particles are decreased to submicron size or even to several tenth angstrom (Å), the particles themselves cannot be observed by an optical microscope, but the region where any defect exists can be clearly observed, since the manner of the light beam reflection differs from that of the other portions where there is no swelling. Even if such defect cannot directly be observed through a microscope, the existence of such defect can be observed as a bright and dark image in the microphotograph.

However, since the conventional ferrofluid used in magnetic flaw detection was exactly a conventional fluid as previously described and is merely held at the portion being bound by the leaked magnetic flux, the fluid begins to flow as soon as the magnetic field applied to the article is removed. Naturally, the swelling of the fluid which indicates the pattern of the defect also disappears.

Accordingly, the defective region becomes unidentifiable as soon as the article to be inspected is removed from the magnetic field.

In view of the drawbacks mentioned above, it is desirable that a ferrofluid be formulated in which a pattern does not disappear once formed even if the article is removed from the magnetic field.

It is also desirable that this ferrofluid contain a photosetting resin or resins used as a carrier into which ferromagnetic particles can be stably dispersed.

The desired ferrofluid could be applied onto the surface of the article to be inspected so as to form a distribution pattern of the ferrofluid corresponding to the defective region of the article or to the magnetic flux pattern formed by the magnetic recording. Subsequently a beam of light having such a specific wave length that is able to set or harden the photosetting resin could be applied onto the surface so as to fix the defect pattern thus formed.

The desired ferrofluid would address the drawbacks encountered in the conventional ferrofluids. It is desirable to provide a ferrofluid which is able to fix and hold a pattern of the ferrofluid corresponding to the pattern of the magnetic flux formed by the defect in the article to be inspected.

The desired ferrofluid would be able to fix and hold the pattern of ferrofluid thus solving the problems of fixation, holding and observation of the pattern of the defect outside the applied magnetic field. However, since the desired ferrofluid would contain a carrier which in itself was a kind of photosetting resin, the swelled portion of the ferrofluid caused by the leaked magnetic field due to any defect in the article might be gentle in its inclination; giving rise to insufficient sharpness in the image of the photomicrograph taken for observation. Thus, it would be desirable to develop a ferrofluid and process for using the same which would obviate all such problems explained above and would provide such a high sensitive photosetting ferrofluid permitting not only fixation of the pattern of the ferrofluid corresponding to the article to be inspected but also to the taking of photomicrographs having very sharp contrast.

SUMMARY OF THE INVENTION

A first embodiment of the present invention to solve one of the problems mentioned above is a photosetting type ferrofluid which is prepared by admixing photosetting resin with ferrofluid in which ferromagnetic particles having an absorbed surfactant or surfactants are dispersed into a carrier.

An improved photosetting type ferrofluid is also proposed as a second embodiment of the present invention, in which the carrier itself is composed at least of a photosetting resin.

A further improved photosetting type ferrofluid having higher sensitivity than that of the second embodiment is also proposed as a third embodiment, in order to obtain higher sharp microphotograph image. This third sensitive photosetting type ferrofluid is prepared by admixing a ferrofluid which consists essentially of a carrier of low viscosity, ferromagnetic particles, a surfactant or surfactants for dispersing the ferromagnetic particles in said carrier with photosetting resin in an amount of at least 25% by volume of the carrier.

When photosetting type ferrofluid of this invention is used for magnetic flaw detection or to visualize a magnetically recorded pattern, the ferrofluid is first applied onto the surface of the article on which a magnetic field has been formed. The ferrofluid is, then, urged to swell by being attracted either by the leaked magnetic flux caused by the defective region or by the variation in the magnetic flux of the recorded magnetic signal. This gives rise to form a distribution pattern of the ferrofluid corresponding to the pattern of the magnetic flux. Next, the article is exposed to a beam of light having a specific wave length sufficient to set or harden the photosetting resin contained in the ferrofluid or added as a carrier; fixing the pattern of the ferrofluid formed by the magnetic flux.

Where sharp photographic images must be obtained, the improved ferrofluid uses a carrier of low viscosity. By virtue of the use of a low viscosity carrier, the ferrofluid swells up with steep inclinations. Subsequently, a light beam of a specific wave length sufficient for setting the photosetting resin added in the ferrofluid as a pattern fixing agent is directed to the fluid so as to fix the pattern formed by the ferrofluid.

Moreover, since the portion having magnetic flux variation can be fixed with steep inclinations, the difference with respect to the state of reflection between the defective or studied portion and the adjacent portions can be heightened as an image having such a sharp contrast which enables the person to observe any minor defects in an article or the magnetically recorded pattern in clearer manner.

BRIEF DESCRIPTION OF THE DRAWING

Attached drawing is a schematic sectional side view showing the internaal defect detected in the steel piece by means of the magnetic flow detection.

DETAILED DESCRIPTION OF THE INVENTION

The photo-setting magnetic fluid according to the first embodiment of the present invention is explained in detail below.

I. The dispersing medium of the ferromagnetic fine particles according to the first embodiment of the present invention becomes unnecessary after it has been coated on a subject body. Thus, the dispersing medium is, preferably, an organic solvent which is comparably volatile at ambient temperature. The solvent is desirably the one which has a vapor pressure less than or equal to 400 mm Mercury at ambient temperature. Solvents having a vapor pressure exceeding this value will be evaporated too rapidly to coat the fine particles on the subject body uniformly and homogeneously.

The solvent employed as the dispersing medium is selected from the group consisting of: (a) hydrocarbons such as n-pentane, cyclohexane, petroleum ether, petroleum benzine, benzene, xylene, toluene and mixtures thereof; (b) halogenated hydrocarbons such as chlorobenzene, dichlorobenzene, bromobenzene and mixtures thereof; (c) alcohols such as methanol, ethanol, n-propanol, n-butanol, isobutanol, benzylalcohol and mixtures thereof; (d) ethers such as diethyl ether, diisopropyl ether and mixtures thereof; (e) aldehydes such as furfural and mixtures thereof; (f) ketones such as acetone, ethyl methyl ketone and mixtures thereof; (g) fatty acid such as acetic acid, acetic anhydride and mixtures thereof and derivatives thereof; and (h) phenols, as well as mixtures of the various solvents.

The surfactant for stably dispersing the ferromagnetic fine particles into the solvent may be selected without limitation from those containing as the main component an unsaturated fatty acid or a fatty acid salt having one or more polar groups selected from the group consisting of $COOH$, $SO_3H$, $PO_3H$ and mixtures thereof; or other surfactants well-known in the art.

As the ferromagnetic fine particle according to the present invention, there can be used a magnetite colloid which is obtained by the well-known wet method. It may be the one which is obtained by grinding the magnetite powder in water, that is, the so-called wet milling method.

Alternately, ferromagnetic oxides can be used such as oxides selected from the group consisting of manganese ferrite other than magnetite, cobalt ferrite, metallic composite ferrites, barium ferrite, and mixtures thereof. Where metallic composite ferrites are employed, they are preferably selected from the group consisting of zinc, nickel and mixtures thereof. Also suitable for use herein are ferromagnetic metals selected from the group consisting of iron, cobalt, rare earth metals and mixtures thereof.

The particle diameter of the ferromagnetic fine particles of the present invention may be in the range of about 0.1 $\mu$m to about 20 Å. The accuracy of examination of magnetic flaws or magnetic recording patterns is improved in proportion to the reduction of the particle diameter of ferromagnetic fine particles, and thus it is preferred to make fine particles where necessary.

The composition of the present invention contains the ferromagnetic fine particles such as those just described in the range of about 1 to about 20% by volume. Where the irradiation by light for curing a photo-setting resin is taken into account, the particles are preferably in a lower concentration.

The photo-setting resin used for the photo-setting type magnetic fluid of the present invention can be selected, by taking the compatibility with the dispersing medium or carrier into consideration from the group of the so-called photosensitive polymers from the group consisting of the following:

(1) Polymers sensitive to electron beams and X-rays selected from the group consisting of polyvinylcinnamate, polyvinyl-p-azide benzoate, epoxidized polyisoprene, polyglycidylmethacrylate, epoxidized polybutadiene, methylvinylsiloxane, polymethylcyclohexane, polyvinylsiloxane, polybutadiene polydiallyl-o-phthalate, polyvinyl chloride, polystyrene, polyacrylamide, polyvinyl ferrocene, polyvinyl carbazole, and mixtures thereof;

(2) Adducts of photopolymerizable monomers and polymer compounds selected from the group consisting of: acrylic acid esters of a polyhydric alcohol, urethane type acrylic acid esters, unsaturated esters of a polyhydric carboxylic acid, unsaturated acid amides, ester or metal salts of an inorganic acid, monomers having an acetylenic unsaturated group, monomers having a glycidyl group, and mixtures thereof;

(3) Simple photo-polymerization systems such as those selected from the group consisting of barium acrylate, methylene blue-sodium p-toluene-sulfinate, and iron salt of acrylamide, N-vinyl carbazole, and mixtures thereof;

(4) Polyvinyl cinnamate and analogous polymers thereof selected from the group consisting of polyvinyl cinnamate, p-methoxycinnamic acid-succinic acid esters, succinic acid esters of an ethylene-vinyl alcohol copolymer, succinic acid esters of glyptal resin, succinic acid esters of an epoxy resin, polyvinylcinnamylidene acetate, polyvinyl benzalacetophenone, polyvinylstyryne pyridinium, a styryne ketone type polymer, and mixtures thereof;

(5) Polymers having diazo and azide groups such as those selected frm the group consisting of polymers having a diazonium salt moiety, polymers having a naphthoquinone diazide moiety, polyazide styrene, polyvinyl-p-azide benzoate, cellulose aceto-3-azide phthalate, and mixtures thereof;

(6) Polymers having other photosensitive groups such as 1,2,3,4-Aziazole type polymers, etc.

(7) Mixtures of a dichromate and a polymer compound, the polymer compound selected from the group consisting of egg white albumin, casein, glue, gelatin, gum arabic, polyvinyl alcohol and mixtures thereof and the chromate, preferably being dichromate.

(8) Diazo and azide compounds and polymer compounds such as p-quinone diamide compounds, diazo resin, polyisoprene, and mixtures thereof.

These photo-sensitive polymers are those which, on being exposed to an irradiating light at a particular wave length, cause photo-setting reaction to occur and the polymer to be cured. It is also within the purview of this invention to improve the light sensitivity of the polymer by the addition of a well-known sensitizer.

II. The photo-setting type magnetic fluid according to the second embodiment of the present invention is explained in detail below.

The dispersing medium or carrier of the ferromagnetic fine particles of the second embodiment of the present invention is a photo-setting type resin and can be selected from the group of the so-called photosensitive polymers as follows:

There can be used functional monomers having a functional group selected from the group consisting of acroyl radicals, ($CH_2$=CHCOO—), methacryloyl radicals ($CH_2$=C($CH_3$)—COO—), acrylamide group ($CH_2$=CH—CONH—), maleic acid diester radicals (—OCOCH=CH—COO—), allyl radicals ($CH_2$=CH—$CH_2$—), vinyl ether radicals ($CH_2$=CH—O—), vinyl thioether radicals ($CH_2$=CH—S—), vinylamino radicals ($CH_2$=CH—NH—), glycidyl radicals (O—$CH_2$—CH—$CH_2$—), acetylenic unsaturated radicals (—C≡C—) and mixtures thereof such as acrylic acid, methacrylic acid, methyl acrylate, methyl methacrylate, butyl acrylate, cyclohexyl acrylate, carbitol acrylate, acrylamide, styrene, acrylonitrile, N-vinylpyrrolidone or the like.

These are roughly divided into the simple polymerization system and the polymer compounds as described below:

(1) Simple photo polymerization system:

Barium acrylate, methylene blue-sodium p-toluenesulfinate, an iron salt of acrylamide, N-vinyl carbazole, etc.

(2) Adducts system with polymer compounds:

Acrylic acid esters of a polyhydric alcohol, urethane type acrylic acid ester, unsaturated esters of a polyhydric carboxylic acid, unsaturated acid amides, esters or metal salts of inorganic acids, monomers having an acetylenic unsaturated group, monomers having a glycidyl group, etc.

Moreover, it can be obtained to get a similar effect by further adding other polymer compounds or photo-sensitive polymers to the photo-sensitive monomers of the simple polymerization system or the adducts system of polymer compounds described above.

The photo-setting type magnetic fluid of the present invention can be obtained by using ultraviolet-curing type resin such as a hydrocarbon type, a fluorine type, a silicone type or the like as well as the aforementioned photo-sensitive polymers. It is also possible to obtain the similar effect by adding well-known sensitizers. These photo-sensitive polymers are those which, on irradiating light at a particular wave length, cause photo-setting polymer to be cured.

The surfactant for stably dispersing the ferromagnetic fine particles into the solvent comprising the photo-setting type resin as mentioned above can be selected from the group consisting of unsaturated fatty acids and salts thereof wherein the fatty acid or salt has one or more polar groups such as COOH, $SO_3H$, $PO_3H$ and mixtures thereof which will bonded by coupling or a salt thereof. Other surfactants well-known in the art such as silicone type surfactants, fluorine type surfactants or the like can also be employed.

As the ferromagnetic fine particles used in this embodiment II there can be used the same fine particles as mentioned in the embodiment I above. The content thereof may be in the range of about 1 to about 30%.

III. The photo-setting type magnetic fluid according to the third embodiment of the present invention is explained in detail below.

In the photo-setting type fluid of this embodiment, the carrier, namely, the dispersing medium used for the ferromagnetic fine particles is an inorganic solvent, an organic solvent or mixture of the two having a vapor pressure less than or equal to about 400 mmHg at 20° C. and a low viscosity. It was confirmed experimentally that the solvent having a vapor pressure of exceeding 400 mmHg at °20 C. will evaporate almost at the same time as coating thus forming an uneven coat and causing difficulty for the observation thereafter. Furthermore, the carrier of the present invention must not prevent curing of a photo-setting type magnetic field on curing process of the photo-setting type magnetic fluid by irradiating UV-rays, and thus it is preferred to dry it during that time.

As the dispersing medium satisfying such conditions, there are mentioned specifically an inorganic solvent such as water or organic solvents selected from the group consisting of alcohols, organic acids, fluorinated solvents, siloxinated solvents and mixtures thereof. The alcohol is preferably selected from the group consisting of methanol, ethanol, butanol and mixtures thereof. The organic acid is preferably selected from the group consisting of acetic acid, formic acid and mixtures thereof. The preferable fluorine type low boiling solvents such as triflon or the like may also be employed. Suitable silicone type low boiling solvents include the mixture of dimethyl polysiloxane and acetone or the like. It is also possible to control the vapor pressure and finally the drying speed of solvents, particularly water, by the addition of an inorganic salt. Suitable salts are selected from the group consisting of sodium chloride, potassium chloride, $Na_2SO_4$ and mixtures thereof.

As the ferromagnetic fine particle of the present invention, there can be used magnetite colloid obtained by the well-known wet method, which may be the same as mentioned in the embodiments 1 and 2. The fine particle content may be in the range of about 1 to about 30%. If the irradiation of light for curing a photo-setting resin is taken into account, the fine particle concentration is preferably in a lower concentration.

The surfactant for stably dispersing the ferromagnetic fine particles mentioned above into the dispersing medium can be selected from those having one or more polar groups such as COOH, $SO_3H$, $PO_3H$ or the like.

In the present invention, a photo-setting type resin is further blended in a magnetic fluid composed of a dispensing medium containing ferromagnetic fine particles having an adsorbed surfactant. The photo-setting type resin can be a photosensitive polymer composed of functional monomers having a functional group selected from the group consisting of acroyl radicals ($CH_2$=CHCOO—), methacryloyl radicals ($CH_2$=C($CH_3$)—COO—), acrylamide radicals ($CH_2$=CH—CONH—), maleic acid diester radicals (—OCOCH=CH—COO—), allyl radicals ($CH_2$=CH—$CH_2$—), vinyl ether radicals ($CH_2$=CH—O—), vinyl thioether radicals ($CH_2=CH-S-$), vinylamino radicals ($CH_2=CH-NH-$), glycidyl radicals ($O-CH_2-CH-CH_2-$), acetylenic unsaturated radicals ($-C\equiv C-$) and mixtures thereof. Suitable polymers are made from monomers selected from the group consisting of acrylic acid, methacrylic acid, methyl acrylate, methyl methacrylate, butyl acrylate, cyclohexyl acrylate, carbitol acrylate, acrylamide, styrene, acrylonitril, N-vinylpyrrolidone and mixtures thereof as well as similar compounds.

These materials are roughly divided into the simple polymerization system and the polymer compounds. Examples of the simple photo polymerization system are compounds selected from the group consisting of barium acrylate, methylene blue- sodium p-toluene-sulfinate, iron salts of acrylamide, N-vinyl carbazole, and mixtures thereof. Examples of adducts system with polymer compounds are compounds selected from the group consisting of acrylic acid esters of a polyhydric alcohol, urethane type acrylic acid esters, unsaturated esters of a polyhydric carboxylic acid, unsaturated acid amides, esters of metal salts of an inorganic acid, monomers having an acetylenic unsaturated group, monomers having a glycidyl group, and mixtures thereof.

Moreover, a similar effect can be obtained by further adding other polymeric compounds or photo-sensitive polymers to the photo-sensitive polymers to the photo-sensitive monomers of the simple polymnerization system or the adducts system of polymer compounds described above.

The photo-setting type magnetic fluid of the present invention can also be obtained by blending ultraviolet-curing type resins such as a hydrocarbon type, a fluorine type, a silicone type or the like as well as the aforementioned photo-sensitive polymers. The photo-setting resin is selected with consideration for the affinity with the dispersing medium of the magnetic fluid as a base. For instance, if the dispersing medium is an aqueous solvent, the resin is preferably an aqueous photo-setting type resin. If the medium is a fluorinated solvent, an organic solvent or a mixed solvent of the two, the resin is preferably a fluorine type photo-setting resin. And if the medium is a silicon type solvent, an organic solvent or a mixed solvent of the two, the resin is preferably a silicon type photo-setting resin.

Suitable photo-sensitizers such as those well known in the art may also be added where further sensitization is required.

The photo-sensitive polymers mentioned above are those which on irradiating light at a particular wave length cause photo-setting reaction to be cured.

EXAMPLE I

The following example of a photosetting ferrofluid comprising a photosetting compound and organic solvent as a carrier and magnetite as a dispersant is described below together with methods of producing the photosetting ferrofluids as described previously in the first embodiment of this invention.

The pH value of 1 liter of an aqueous solution containing 1 mole of each of ferrous sulfate and ferric sulfate was first adjusted to 11 or more by adding an aqueous 6N-NaOH solution thereto, and then the solution was subjectd to maturing for 30 minutes at 60° C. to obtain a magnetite collioid (wet method). The pH of the magnetite slurry was, then, adjusted to between 2 and 3 by the addition of 3N hydrochloric acid while maintaining the temperature at 60° C. Seventy grams of petroleum sodium sulfonate was, then, added to the magnitite slurry. The sulfonate served as a surfactant for stably dispersing colloidal particles. The obtained mixture was, then, agitated for 30 minutes.

The stirring and agitation was, then, discontinued and the magnetite particles allowed to aggregate and settles. The supernatant was decanted and water was poured into the residue to wash it. Water washing was repeated several times to remove any residual electrolytes. After water washing, the residual solution was extracted with hexane which served as a low-boiling solvent. As a result of the extraction, the magnetite particles were transferred into the hexane layer thereby obtaining an intermediate carrier in which ferromagnetic fine particles having their surface coated with the surfactant were dispersed. The intermediate carrier was then subjected to centrifugal separation using a centrifugal force of 8000 G for 20 minutes to settle and separate large magnetite particles. The particle diameter of the ferromagnetic fine particles remaining in the supernatant liquid was 100 to 150 A. Such centrifugal separation of the intermediate carrier enabled the arbitrary adjustment of the particle size distribution of the ferromagnetic fine particles, and had a particularly advantage with respect to an increase in the concentration of the fine particles.

The supernatant was, then, transferred into a rotary evaporator kept at 90° C. where hexane was removed by evaporation. Ten grams of the powdered magnetite fine particles thus obtained were again dispersed in 100 ml of hexane and, then, mixed with 100 ml of a 70% xylene solution of cyclized polyisoprene rubber (commercially available under the tradename OMR-85, produced by Tokyo Ohka Co., Ltd.). The material was a photosensitive polymer. The mixture of magnetite fine particles and xylene-polyisoprene rubber was subjected to treatment in a centrifugal separator of 60 minutes under a centrifugal force of 8000 G to remove any non-dispersing solid.

Consequently, a photosetting ferrofluid comprising the ferromagnetic magnetite fine particles, which were extremely stably dispersed in the mixed solution of xylene and cyclized polyisoprene rubber through the surfactant, was obtained.

EXAMPLE II

The following is an example of a photosetting ferrofluid made according to the first embodiment of the present invention.

A magnetite colloidal slurry was obtained by a wet method in the same way as that employed in Example I.

Seventy grams of sodium oleate which served as the surfactant was then added to the slurry, followed by agitation for 30 minutes. The pH of the slurry was adjusted to between 2 and 3 while maintaining the slurry temperature at 60° C. by adding 3N hydrochloric acid.

An intermediate carrier in which the ferromagnetic fine particles having the surfaces coated with the surfactant were dispersed was formed by the same treatment as that conducted in Example I. A photosetting ferrofluid comprising the ferromagnetic magnetite fine particles, which were extremely stably dispersed in the mixed solution of xylene and cyclized polyisoprene rubber through the surfactant, was obtained from the intermediate carrier in the manner described previously in Example I.

EXAMPLE III

The following is an example of a photosetting ferrofluid made according to the first embodiment of the present invention.

A magnetite colloidal slurry was obtained by a wet method in the same manner as that employed in Example 1.

After the magnetite particles had been aggregated and settled, the supernatant liquid was removed, and water was poured into the residue so as to wash it. Water washing was repeated several times to remove residual electrolytes. The washed material was filtered off and dried to obtain powdered magnetite.

Ten grams of the dried magnetite was mixed with 100 ml of a xylene solution (70%) of a cyclized poolyisoprene rubber which was a photosensitive polymer as described previously in Example I. One gram of a cationic surfactant (commercially available un the trademark KS-43, produced by Kao Soap Co., Ltd.) was, then, added to the obtained mixture. The mixture was treated in a ball mill for 3 hours and then subjected to treatment in a centrifugal force of 8000 G to remove any non-dispersing solid.

The photosetting ferrofluid thus produced comprised the ferromagnetic magnetite fine particles, which are extremely stably dispersed in the mixed solution of xylene and cyclized polyisoprene rubber through the surfactant.

EXAMPLE IV

The following is an example of a photosetting ferrofluid made according to the first embodiment of the present invention.

A magnetite colloidal slurry was obtained by a wet method in the same way as that employed in Example I.

An aqueous solution of 3N hydrochloric acid was added to the obtained slurry so as to adjust the pH thereof to a value between 7 to 8. Seventy grams of a silane coupling agent (commercially available under the tradename A-1100, produced by Nippon Yunika Co., Ltd.) which served as a first surfactant was then added to the magnetite slurry, followed by agitation for 30 minutes. After agitation, 70 g of sodium oleate, which serviced as a second surfactant, was then added to the obtained mixture, followed by agitation for 1 hour.

After electrolytes had been removed by washing with water by the same treatment outlined in Example I, the low-boiling solvent hexane was added to the residue to obtain an intermediate carrier in which ferromagnetic fine particles having their surfaces coated with the surfactants were dispersed.

A photosetting ferrofluid comprising the ferromagnetic magnetite fine particles, which were extremely stably dispersed in the mixed solution xylene as a carrier and cyclized polyisoprene rubber which was a photosensitive polymer through the surfactant, was obtained from the intermediate carrier.

EXAMPLE V

Tests of magnetic flaw detection were performed for steel plate by using the photosetting ferrofluids obtained in Examples 1 to 4.

A steel plate having a known internal defect 1 placed several micrometers below the surface of the steel plate. The defect, about 2 mm long and 50 mm wide, as schematically shown in FIG. 1, was used as each test piece 2.

The test piece 2 was placed in a magnetic field of 13K gauss and a photosetting ferrofluid 3 was applied onto the surfaces thereof by a brush. As a result, the ferromagnetic particles were locally concentrated by the action of a leakage flux 4 produced near the position immediately above the internal defect 1 in the test piece 2. A swelling phenomenon of the photosetting ferrofluid 3 along the internal defect 1 was produced as shown in the figure.

The swelling phenomenon disappeared when the test piece 2 was taken out of the magnetic field, and the phenomenon was again observed when the test piece 2 was returned to the magnetic field. Ultraviolet rays having wave lengths of about 400 to 500 nm were applied to the photosetting ferrofluid 3 showing the swelling phenomenon. The photosetting ferrofluid 3 was cured over a period of about 1 minute so that a state showing the internal defect 1 could be fixed as it was.

When a coating of the curved photosetting ferrofluid 3 was separated from the test piece 2 and then observed by a microscope, the state of the internal defect showing a needle-like shadow could be correctly observed.

EXAMPLE VI

The following is an example of a photosetting ferrofluid composition according to the second embodiment of this invention.

The pH value of 1 liter of an aqueous solution containing 1 mole of each of ferrous sulfate and ferric sulfate was first adjusted to 11 or more by adding an aqueous 6N sodium hydroxide solution thereto. The iron solution was subjected to maturing for 30 minutes at 60° C. to obtain a magnetite colloid (wet method). Seventy grams of a silane coupling agent (commercially available under the tradename SH-6040, produced by Toray Silicone Co., Ltd.) was used as a surfactant for stably dispersing colloidal particles. The silane coupling agent added to the magnetite slurry, and the obtained mixture was then agitated for 30 minutes.

The magnetite particles were allowed to aggregate and settle after agitation. The supernatant was removed, and water was poured into the residue so as to wash it. Water washing was repeated several times to remove electrolytes.

After water washing, the washed solution was extracted with the low-boiling solvent, hexane. As a result, the magnetite particles were transferred into the hexane layer thereby obtaining an intermediate carrier in which ferromagnetic fine particles having their surfaces coated with the surfactant were dispersed. The intermediate carrier thus obtained was then subjected to centrifugal separation using a centrifugal force of 8000 G for 20 minutes to settle and separate large magnetite particles. The particle diameter of the ferromagnetic fine particles remaining in the supernatant liquid was 100 to 150 Å.

Such centrifugal separation of the intermediate carrier of low viscosity enabled the arbitrary adjustment of the particle size distribution of the ferromagnetic fine particles, and had a particular advantage with respect to any increase in the concentration of the fine particles.

The supernatant was then transferred into a rotary evaporator kept in 90° C. where the hexane was removed by evaporation. Ten grams of the powdered magnetite fine particles obtained through evaporation was mixed with 100 ml of methanol and 100 ml of a photosensitive polymer, epoxyacrylate (commercially available under the tradename V-5502, produced by Dai-Nippon Ink Inc.,).

The obtained mixture was placed in an evaporator kept at 70° C. so that the methanol was removed by evaporation, and the residue was then subjected to treatment in a centrifugal separator for 60 minutes under a centrifugal force of 8000 G to remove any non-dispersing solid.

Consequently, a photosetting ferrofluid comprising the ferromagnetic magnetite fine particles, which were extremely stably dispersed in a photosetting resin through the surfactant, was obtained.

EXAMPLE VII

The following is an example based on the second embodiment of the present invention.

The pH value of 1 liter of an aqueous solution containing 1 mole of each of ferrous sulfate and ferric sulfate was first adjusted to 11 or more by adding an aqueous 6N sodium hydroxide solution thereto. The iron solution was, then, subject to maturing for 30 minutes at 60° C. to obtain a magnetite colloid (wet method). Seventy grams of an anionic surfactant (commercially available under the tradename Salcosinate LH, produced by Nikko Chemicals Co., Ltd.) was employed as a surfactant for stably dispersing colloidal particles and was added to the magnetite slurry obtained mixture was then agitated for 30 minutes.

After agitation the magnetite particles were allowed to aggregate and settle. The supernatant liquid was decanted and water was poured into the residue so as to wash it. Water washing was repeated several times to remove electrolytes. After water washing, the residual solution was extracted with thinner as a low-boiling point solvent and allowed into water and thinner layers.

As a result, the magnetite particles were transferred into the thinner layer thus creating an intermediate medium in which ferromagnetic fine particles having the surfaces coated with the surfactant were dispersed. The obtained intermediate carrier was then subjected to centrifugal separation using a centrifugal force of 8000 G for 20 minutes to settle and separate large magnetite particles. The particle diameter of the ferromagnetic fine particles remaining in the supernatant liquid was 100 to 150 Å.

Such centrifugal separation of the intermediate carrier enabled the arbitrary adjustment of the particle size distribution of the ferromagnetic fine particles, and had a particular advantage with respect to an increase in the concentration of the fine particles. The supernatant liquid was then transferred into a rotary evaporation kept at 90° C. where the solvent was removed by evaporation.

Ten grams of the powdered magnetite fine particles thus obtained was mixed with 100 ml of thinner (produced by Dai-Nippon Ink Inc.,) and 100 ml of an ultraviolet-curing resin (commercially available under the tradename Unidick 17-8249, produced by Dai-Nippon Ink Inc.,). The obtained mixture was placed in an evaporation, and the residue was then subjected to treatment in a centrifugal separator for 60 minutes under a centrifugal force of 8000 G to remove any non-dispersing solid.

Consequently, a photosetting ferrofluid comprising the ferromagnetic magnetite fine particles which were extremely stably dispersed in a photosetting resin through the surfactant was obtained.

EXAMPLE VIII

The following is an example produced according to the second embodiment of this present invention.

The pH value of 1 liter of an aqueous solution containing 1 mole of each of ferrous sulfate and ferric sulfate was first adjusted to 11 or more by adding an aqueous 6N sodium hydroxide solution thereto. The resulting iron solution was subjected to maturing for 30 minutes at 60° C. to obtain a magnetite colloid (wet method). Ethanol was then added to the magnetite slurry solution to a volume of about 3 times the volume of the slurry. Seventy grams of a fluorine surfactant having the formula $CF_3(CF_2)_7CH_2CH_2Si(OCH_3)_3$ (commercially available under the tradename XC95-470, produced by Toshiba Silicone Co., Ltd.) was employed as a surfactant for stably dispersing colloidal particles and was added to the magnetite slurry. The obtained mixture was then agitated for 30 minutes.

After agitation, the mixture has been held still until the magnetite particles were allowed to aggregate and settle. The supernatant liquid was decanted. Water was repeatedly poured into the residue to wash it and remove electrolytes. After water washing, the solvent was removed by filtration, and the residue was well dried. The magnetite particles were then poured into a low-boiling point fluorine solvent (commercially available under the tradename Triflone, produced by Central Glass Co., Ltd.).

As a result, an intermediate carrier in which ferromagnetic fine particles having their surfaces coated with the surfactant dispersed in the low-boiling point fluorine solvent was obtained. The intermediate carrier thus obtained was, then, subjected to centrifugal separation using a centrifugal force of 8000 G for 20 minutes to settle and separate large magnetite particles. The particle diameter of the ferromagnetic fine particles remaining in the supernatant liquid was 100 to 150 Å.

Such centrifugal separation of the intermediate carrier of low viscosity enabled the arbitrary adjustment of the particle size distribution of the ferromagnetic fine particles, and had a particular advantage with respect to an increase in the concentration of the finer particles.

The supernatant liquid was then transferred into a rotary evaporator kept at 90° C. The low-boiling point fluorine solvent was removed by evaporation.

One gram of the powdered magnetite fine particles thus obtained was mixed with 100 ml of a low-boiling point fluorinated solvent and 10 ml of an ultraviolet-curing fluorine resin (commercially available under the tradename DEFENSA, NS-1, produced by Dai-Nippon Ink Inc.,). The resulting mixture was placed in an evaporator kept at 90° C. where the low-boiling fluorinated solvent was removed by evaporation. The residue was then subjected to treatment in a centrifugal separator for 60 minutes under a centrifugal force of 8000 G to remove any non-dispersing solid.

Consequently, a fluorine photosetting ferrofluid comprising the ferromagnetic magnetite fine particles, which were extremely stably dispersed in a photosetting resin through the surfactant, was obtained.

EXAMPLE IX

The following is an example prepared according to the second embodiment of the present invention.

The pH value of 1 liter of an aqueous solution containing 1 mole of each of ferrous sulfate and ferric sulfate was first adjusted to greater than or equal to 11 by adding an aqueous 6N sodium hydroxide solution thereto. The iron solution was subjected to maturing for 30 minutes at 60° C. to obtain a magnetite colloid (wet method). The pH of the resulting magnetite slurry was, then, adjusted to a value between 2 and 3 by the addition of 3N hydrochloric acid while the slurry solution was maintained at 60° C. Seventy grams of petroleum sodium sulfonate was employed as a first surfactant for stably dispersing colloidal particles was then added to the magnetite slurry. The resulting mixture was then agitated for 30 minutes.

The magnetite particles in the mixture were permitted to aggregate and settle and the supernatant liquid was decanted. The residue was washed with water several times to remove electrolytes. After water washing, the solution was extracted using the low-boiling solvent, hexane. The magnetite particles were transferred into the hexane layer to obtain an intermediate carrier in which ferromagnetic fine particles having the surfaces coated with the first surfactant were dispersed.

The obtained intermediate carrier was then subjected to centrifugal separation using a centrifugal force of 8000 G for 20 minutes to settle and separate large magnetite particles. The particle diameter of the ferromagnetic fine particles remaining in the supernatant was 100 to 150 Å. Such centrifugal separation of the intermediate carrier of low viscosity enabled the arbitrary adjustment of the particle size distribution of the ferromagnetic fine particles, and had a particular advantage with respect to an increase in the concentration of the finer particles.

The supernatant liquid was then transferred into a rotary evaporator kept at 90° C. to remove the hexane by evaporation. 10 grams of the powdered magnetite fine particles thus obtained was again dispersed in 100 ml of hexane, and an ultraviolet-curing silicone A solution (commercially available under the tradename KNS-5002A, produced by Shin-etsu Chemical Industry Co., Ltd.) which served as a carrier was then added to the mixture. Carboxylated silicone (Sample 555, produced by Toray Silicone Co., Ltd.) which served as a second surfactant was then added to the obtained mixture in a weight ratio of 10% of the ultraviolet-curing silicone A solution. The obtained mixture was treated by an evaporator to evaporate the hexane with a low boiling point.

As a result, a fluid comprising the ferromagnetic magnetite fine particles, which were very stably dispersed in the ultraviolet-curing silicone A solution as the carrier through the surfactants, was obtained. An ultraviolet-curing silicone A solution as the carrier through the surfactants, was obtained. An ultrviolet-curing silicone B solution (commercially available under the tradename KNS-5002B, produced by Sin-etsu Chemical Industry Co., Ltd.) was added to the thus-obtained fluid in a weight ratio to the ultraviolet-curing silicone A solution of 1:1 to produce a ultraviolet-curing silicone ferrofluid.

EXAMPLE X

A test of magnetic flaw detection was performed for a steel plate by using the photosetting ferrofluid obtained in Example IX.

A steel plate having a known internal defect 1 which was placed several micrometers below the surface of the steel and was about 2 mm long and 50 mm wide, as schematically shown in FIG. 1 was used as a test piece 2.

The test piece 2 was placed in a magnetic field of 13K gauss and a photosetting ferrofluid 3 was applied onto the surfaces thereof by a brush. As a result, the ferromagnetic particles were locally concentrated by the action of a leakage flux 4 produced near the position immediately above the internal defect 1 in the test piece 2, with producing a swelling phenomenon of the photosetting ferrofluid 3 along the internal defect 1, as shown in the figure. The swelling phenomenon disappeared when the test piece 2 was taken out of the magnetic field, and the phenomenon was again observed when the test piece 2 was returned to the magnetic field.

When a coating of the cured photosetting ferrofluid 3 was separated from the test piece 2 and then observed by a microscope, the state of the internal defect showing a needle-like shadow could be correctly observed.

EXAMPLE XI

The following is an example of the present invention as set forth in the third embodiment.

The pH value of 1 liter of an aqueous solution containing 1 mole of each of ferrous sulfate and ferric sulfate was first adjusted to 11 or more by adding an aqueous 6N sodium hydroxide solution thereto, and then the iron solution was subjected to maturing for 30 minutes at 60° C. to obtain a magnetite colloid (wet method). 3N-HCl was then added to the magnetite slurry solution kept at 60° C. so as to adjust the pH value thereof to a value within 2 to 3. 70 grams of a saline coupling agent (commercially available from Toray Silicone Co., Ltd.) which was employed as a first surfactant for stably dispersing colloidal particles was then added to the magnetic slurry. The mixture thus obtained was then agitated for 30 minutes.

After agitation, the mixture has been held still and the magnetite particles were permitted to aggregate and settle. The supernatant liquid was removed, and the residue was washed several times to remove electrolytes. After water washing, the solution was extracted with the low-boiling solvent, hexane to permit accumulation of the magnetite particles in the hexane layer to obtain an intermediate carrier in which ferromagnetic fine particles having the surfaces coated with the first surfactant were dispersed. The obtained intermediate carrier was then subjected to centrifugal separation using a centrifugal force of 8000 G for 20 minutes to settle and separate large magnetite particles. The particle diameter of the ferromagnetic fine particles remaining in the supernatant was 100 to 150 A. Such centrifugal separation of the intermediate carrier of low viscosity enabled the arbitrary adjustment of the particle size distribution of the ferromagnetic fine particles, and had a particular advantage with respect to an increase in the concentration of the finer particles The supernatant liquid was then transferred into a rotary evaporator kept at 90° where the hexane was removed by evaporation. Ten grams of the powdered magnetite fine particles thus obtained was again poured into hexane to be dispersed therein. Two hundred ml of an aqueous carrier solution in which 3 g of sodium oleate was dissolved was added to the obtained solution and well mixed. The sodium oleate was employed as a second surfactant. The mixture was then transferred to a separating funnel and then held still to separate the solution into water and hexane layers.

The addition of the sodium oleate allowed a hydrophilic second surfactant layer to be formed in a layer on each of the surfaces of the lipophilic ferromagnetic fine particles previously coated with the silane coupling agent serving as the first surfactant. Thus the ferromagnetic fine particles could maintain their dispersebility in the aqueous solvent.

As a result, a ferrofluid in which the ferromagnetic fine particles capable of stable dispersement in the aqueous solvent was obtained. One hundred ml of a water-soluble photosetting resin (commercially available under the trade designation 17-824EM, produced by Dai-Nippon Ink & Chemicals, Inc.) was added to the obtained ferrofluid, and the solid impurities were centrifugally separated to obtain a photosetting ferrofluid which contained water as a carrier and had a low viscosity (5 cp).

EXAMPLE XII

A magnetite colloid was obtained by the wet method employed in Example 1. Ethanol was then added to the magnetite slurry solution in a volume of about 3 times the volume of the slurry solution. Seventy grams of a fluorine surfactant (commercially available under the tradename XC95-470, produced by Toray Silicone Co., Ltd.) was employed as a surfactant for stably dispersing colloidal particles. The material was then added to the magnetite slurry, and the mixture thus obtained was then agitated for 30 minutes.

The magnetite particles in the mixture were then allowed to aggregate and settle, and the resulting supernatant liquid was removed. The residue was washed with water several times to remove electrolytes. After water washing, the solvent was removed by filtration, and the residue was well dried. The dried magnetite was then poured into a low-boiling point fluorine solvent (commercially available under the trademark Triflone, produced by Central Glass Co., Ltd.).

As a result, an intermediate carrier in which ferromagnetic fine particles having their surfaces coated with the surfactant dispersed in the low-boiling point fluorine solvent was obtained. The intermediate carrier was then subjected to centrifugal separation using a centrifugal force of 8000 G for 20 minutes to settle and separate large magnetite particles. The particle diameter of the ferromagnetic fine particles remaining in the supernatant was 100 to 150 Å.

Ten millileters of an ultraviolet-curing fluorine resin (commerically available under the tradename DEFENSA, NS-1, produced by Dai-Nippon Ink Co. Ltd.) was added to the supernatant liquid and an ethanol carrier was also added thereto in a volume of 20 ml which was 2 times the volume of the ultraviolet-curing fluorine resin and well mixed therewith.

The obtained mixture was then subjected to treatment in a centrifugal separator for 60 minutes under a centrifugal force of 8000 G to remove any non-dispersing solid. The resulting material was a photosetting fluorine ferrofluid of low viscosity (5 cp) was obtained.

EXAMPLE XIII

An aqueous magnetite colloidal solution was obtained by a wet method in the manner described in Example I. The magnetite particles were permitted to aggregate and settle, after which the supernatant was removed. The residue was washed with water several times to remove electrolytes. After water washing, 500 ml of dimethylsiloxane (commercially available under the tradename SH200, produced by Toray Silicone Co., Ltd.) 1 liter of acetone, and 70 g of a silicone surfactant (commercially available under the tradename X-24-3504, produced by Shin=etsu Chemical Industry Co., Ltd.), were added to 1 liter of the magnetite slurry. The resulting mixture was agitated for 30 minutes.

The mixture was then transferred into a separating funnel and then held still to separate it into a supernatant and water layer which were separated. Consequently, the magnetite particles were transferred to a solution comprising dimethylsiloxane and acetone creating an intermediate carrier in which ferromagnetic fine particles having their surfaces coated with the silicone surfactant were dispersed. The intermediate carrier was subjected to centrifugal separation for 20 minutes using a centrifugal force of 8000 G to settle and separate large magnetite particles. The particle diameter of the ferromagnetic fine particles remaining in the supernatant liquid between 100 Å and 150 Å. The supernatant liquid was then transferred into a rotary evaporator kept at 90° C. where the dimethylsiloxane and acetone were removed by evaporation.

Ten grams of the powered magnetite fine particles thus obtained was dispersed in a mixture 100 ml of acetone. One hundred milliliters of each of ultraviolet-curing silicone resin solutions (commercially available under the tradename KNS-5002A and KNS-5002B, produced by Shin-etsu Chemical Industry Co., Ltd.) was added to the magnetite-solvent mixture and well mixed therewith. The obtained mixture was subjected to centrifugal separation for 60 minutes with a centrifugal force of 8000 G to remove any non-dispersing solid.

As a result, a photosetting silicone ferrofluid having a viscosity of 10 cp was obtained containing a stable dispersion of the ferromagnetic magnetite particles in the silicone carrier solution and the ultraviolet-curing silicone resin.

EXAMPLE XIV

The volume of the water added as a carrier in Example 1 was changed to 100 ml, 200 ml and 300 ml. As a result, three photosetting ferrofluids, which contained water as a carrier and in which the mixing ratios of photosetting resin to water solvent were 1:1, 1:2 and 1:3, respectively, were obtained. A comparative test of magnetic flaw detection was performed by using the three fluids according to the procedure outlined previously. A stainless steel plate having an internal defect of 200 mm wide, 1 cm long, and several mm deep was used as test piece.

The first photosetting ferrofluid having a mixing ratio of 1:1 had a viscosity of 30 cp. The internal defect was observable but the image obtained was not clear. Where a mixing ratio of 1:2 was used, the resulting material has a viscosity of 5 cp and the internal defect could be clearly observed. Where a mixing ratio of 1:3 was used the resulting ferrofluid had a viscosity of 2 cp and was unable to coat the steel plate uniformly. Thus the third photosetting ferrofluid was unsuitable. As a result, it can be said that the optimal concentration of photosetting ferrofluid in water is about 33% by weight.

EXAMPLE XV

The amount of the ethanol added as a carrier to 10 ml of the ultraviolet-curing fluorine resin (commercially available under the tradename DEFENSA NS-1, produced by Dai-Nippon Ink Co., Ltd.) was changed to 10 ml, 20 ml and 30 ml to obtain three photosetting ferrofluids in which mixing ratios of the photosetting resin to the ethanol solvent were 1:1, 1:2 and 1:3, respectively. A comparative test of magnetic flaw detection was performed by using the three ferrofluids in the same way as that employed in Example 14.

The photosetting ferrofluid having a mixing ratio of 1:1 had a viscosity of 20 cp. The internal defect was observable but the image obtained was not clear. The photosetting ferrofluid having a mixing ratio of 1:2 had a viscosity of 5 cp. The internal defect could be clearly observed. The photosetting ferrofluid having a mixing ratio of 1:3 had a viscosity of 1 cp. The resulting fluid did not provide a uniform coating on the plate was, thus, unsuitable.

Thus, the amount of photosetting resin which can be mixed with water to yield optimal results is about 33% by weight.

EXAMPLE XVI

The amounts of dimethylsiloxane and acetone to be added as carriers relative to 200 ml of a solution comprising 100 ml of each of two ultraviolet-curing silicone resin solutions (KNS-5002B, produced by Shin=etsu Chemical Industry Co., Ltd.) were changed to the three amounts described below. (1) 200 ml of mixed solvent comprising 100 ml of dimethylsiloxane and 100 ml of acetone (2) 400 ml of a mixed solvent comprising 200 ml of dimethylsiloxane and 200 ml of acetone (3) 600 ml of a mixed solvent comprising 300 ml of dimethylsiloxane and 300 ml of acetone Consequently, three photosetting ferrofluids, which respectively comprised the photosetting resin and the mixed solvents in the ratios of 1:1, 1:2 and 1:3 (resin to solvent), were obtained. A comparative test of magnetic flaw detection was performed by using the three ferrofluids in the same way as employed in Example 14.

The first photosetting ferrofluid with a mixing ratio of 1:1 had a viscosity of 37 cp. The internal defect was observable but the obtained image was not clear. The second photosetting ferrofluid had a viscosity of 10 cp. Its use yielded an extremely clear image. The third photosetting ferrofluid had a viscosity of 5 cp and was unable to coat the test plate evenly.

Thus, it can be seen that optimal results are obtained when the amount of photosetting resin mixed with water solvent is about 33% by weight.

The present invention enables a photosetting resin to be mixed with a ferrofluid which is used for testing defects in a test piece having magnetism or testing a magnetically recorded pattern or a photosetting resin to be used as a carrier in a ferrofluid in which ferromagnetic fine particles are dispersed. In addition, since at least 25% by volume of a photosetting resin is mixed with the carrier, the pattern of a ferrofluid which is formed corresponding to any change in the magnetic flux of a test piece can be fixed by applying light thereto, and an extremely sharp and high contrast image can be maintained, it enabling significant improvements in the field of magnetic flaw detection and micro-tests for magnetic recording media.

Having, thus described the present invention, what is claimed is:

1. A photosetting ferrofluid composition consisting essentially of:
   a dispersion medium consistingg essentially of a silicone-containing low boiling point solvent having a vapor pressure below about 400 mm Hg at 20° C.;
   ferromagnetic particles, said particles having a particle size between about 0.1 μm and about 20 Å;
   silicone-containing surfactant; and
   a silicone-containing photosetting resin admixed therein.

2. The photosetting ferrofluid composition of claim 1 wherein the viscosity of the dispersion medium is equal to or below about 37 cp at room temperature.

3. The photosetting ferrofluid composition of claim 1 wherein the dispersion medium contains at least 25% by volume silicone-containing photosetting resin, and wherein said ferromagnetic particles are present in an amount between about 1% and about 30% by volume of the composition.

4. The photosetting ferrofluid composition of claim 1 wherein said silicone-containing photosetting resin is selected from the group consisting of methylvinylsiloxane, polyvinylsiloxane, and mixtures thereof.

5. The photosetting ferrofluid composition of claim 1 wherein said dispersion medium is selected from the group consisting of chemicals having the general formula:

$$R-OH;$$

$$H_3C-\underset{\underset{O}{\|}}{C}-R';$$

$$R''-\underset{\underset{O}{\|}}{C}-OH;$$

and mixtures thereof, wherein R is a hydrocarbon radical having between 1 and 6 carbon atoms, R' is a methyl group or an ethyl group, and R" is a radical selected from the group consisting of hydrogen or a methyl group.

* * * * *